(12) United States Patent
Hansen et al.

(10) Patent No.: US 7,940,047 B2
(45) Date of Patent: May 10, 2011

(54) MICROCONTROLLER SYSTEM FOR IDENTIFYING RF COILS IN THE BORE OF A MAGNETIC RESONANCE IMAGING SYSTEM

(75) Inventors: John W. Hansen, Maple (CA); Joshua L. Richmond, Toronto (CA); Han Wang, Toronto (CA); Gal Sela, Toronto (CA)

(73) Assignee: Sentinelle Medical, Inc., Toronto (CA)

( * ) Notice: Subject to any disclaimer, the term of this patent is extended or adjusted under 35 U.S.C. 154(b) by 242 days.

(21) Appl. No.: 12/277,035

(22) Filed: Nov. 24, 2008

(65) Prior Publication Data

US 2009/0149737 A1    Jun. 11, 2009

Related U.S. Application Data

(60) Provisional application No. 60/989,898, filed on Nov. 23, 2007, provisional application No. 60/989,904, filed on Nov. 23, 2007.

(51) Int. Cl.
*G01V 3/00* (2006.01)

(52) U.S. Cl. ......................................... 324/322; 324/318

(58) Field of Classification Search .......... 324/300–322; 600/407–445; 333/219–235
See application file for complete search history.

(56) References Cited

U.S. PATENT DOCUMENTS

| | | | |
|---|---|---|---|
| 2,964,598 A * | 12/1960 | Parker | 379/347 |
| 5,461,314 A | 10/1995 | Arakawa et al. | |
| 5,551,430 A | 9/1996 | Blakeley et al. | |
| RE36,495 E * | 1/2000 | Blackeley et al. | 600/410 |
| 6,362,622 B1 | 3/2002 | Stauber et al. | |
| 6,437,567 B1 * | 8/2002 | Schenck et al. | 324/318 |
| 6,545,475 B2 | 4/2003 | Kroeckel et al. | |
| 6,816,266 B2 * | 11/2004 | Varshneya et al. | 356/477 |
| 6,873,872 B2 * | 3/2005 | Gluckman et al. | 607/2 |
| 6,925,328 B2 * | 8/2005 | Foster et al. | 607/9 |
| 7,692,427 B2 * | 4/2010 | Lee et al. | 324/322 |
| 7,714,581 B2 * | 5/2010 | Erickson et al. | 324/322 |
| 7,714,583 B2 * | 5/2010 | Zhu et al. | 324/322 |
| 2005/0159661 A1 * | 7/2005 | Connelly et al. | 600/410 |

* cited by examiner

*Primary Examiner* — Brij B Shrivastav
(74) *Attorney, Agent, or Firm* — Quarles & Brady LLP

(57) ABSTRACT

A method and apparatus for identifying local RF coils in a MR system includes a microcontroller that is provided in the bore of the system. The microprocessor determines when local RF coils are connected, identifies the coils, and provides the information to an MR scanner. The controller is shielded to prevent electromagnetic interference.

13 Claims, 7 Drawing Sheets

US 7,940,047 B2

MICROCONTROLLER SYSTEM FOR IDENTIFYING RF COILS IN THE BORE OF A MAGNETIC RESONANCE IMAGING SYSTEM

CROSS-REFERENCE TO RELATED APPLICATIONS

This application claims the benefit of U.S. Provisional Application No. 60/989,898, filed Nov. 23, 2007, and U.S. Provisional Application No. 60/989,904, filed Nov. 23, 2007, which are hereby incorporated by reference.

FIELD OF THE INVENTION

The field of the invention relates to local radiofrequency (RF) coils used in magnetic resonance imaging (MRI), and more particularly to an interface for identifying RF coils and coil configurations in magnetic resonance imaging equipment.

BACKGROUND OF THE INVENTION

When a substance such as human tissue is subjected to a uniform magnetic field (polarizing field B0), the individual electromagnetic moments of the excited nuclei in the tissue attempt to align with this polarizing field. If the substance, or tissue, is subjected to a magnetic field (excitation field B1) that is in the x-y plane and that is near the Larmor frequency, the net aligned moment, Mz, may be rotated, or "tipped", into the x-y plane to produce a net transverse magnetic moment Mt. A signal is emitted by the excited nuclei or "spins", after the excitation signal B1 is terminated as the nuclei precess about B0 at their characteristic Larmor frequency. This signal may be received and processed to form an image.

When utilizing these magnetic resonance "MR" signals to produce images, magnetic field gradients (Gx, Gy and Gz) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. The MR signals acquired with an MRI system are signal samples of the subject of the examination in Fourier space, or what is often referred to in the art as "k-space". Each MR measurement cycle, or pulse sequence, typically samples a portion of k-space along a sampling trajectory characteristic of that pulse sequence.

MRI systems constructed for acquiring MR signals typically include a superconducting magnet provided in a toroidal housing including a bore that is dimensioned to receive a patient to be imaged. The magnet produces the polarizing field B0 axially through the bore, and whole body radio frequency and gradient coils typically surround the bore. In operation, a patient is transported to the bore on a wheeled or otherwise movable patient transport. A patient support is provided on the transport, and this support can be selectively inserted into the bore for imaging, and subsequently retracted.

When performing scans of a selected anatomy of the patient, such as the breast, head or heart, local RF coils configured for the selected anatomy are commonly positioned in the bore with the patient. To provide flexibility for image acquisition, it is desirable to allow medical personnel to select specific RF coil configurations, and to selectively position these RF coils adjacent the anatomy of interest where needed, to allow for the acquisition of a variety of different views. When using a variety of coils and coil connectors however, it is important for the MRI system to be able to identify the RF coil configurations used, as well as their location, prior to a scan. Identification and verification of the coil, however, is complicated by the electromagnetic interference produced by the MRI system itself. The present invention addresses these issues.

SUMMARY OF THE INVENTION

In one aspect of the invention, an interface circuit for use in bore in a magnetic resonance imaging system is provided. The interface circuit is electrically connected to circuitry in the magnetic resonance imaging system to enable communications between the interface circuit and the magnetic resonance imaging system, and includes a controller, an isolation circuit electrically connected to the controller to isolate the controller from noise produced in the magnetic resonance imaging system, and a feedthrough capacitor circuit filtering input and output lines to the controller. The controller, the isolation circuit, and the feedthrough capacitor circuit are each positioned in a shielded compartment, such that electromagnetic interference is sufficiently minimized to allow communication signals to be transmitted between the microcontroller and the magnetic resonance system when the interface circuit is used in the bore of the magnetic resonance imaging system.

In another aspect of the invention, a patient support for use in a magnetic resonance imaging system is provided. The patient support includes a structure for supporting an anatomy of interest of a patient to be imaged, a connector for coupling an RF coil adjacent the anatomy of interest for imaging, and an interface circuit electrically connected to the connector. The interface circuit includes a controller programmed to sense when an RF coil or coils is coupled to the connector, and to read an identifier associated with the RF coil. The controller circuit is shielded from electromagnetic interference produced by the magnetic resonance imaging system and from currents induced in the conductors, and is programmed for a variety of purposes such as signal processing algorithms, or to determine whether the RF coil connected is suitable for use with a previously established coil identification code. The coil identification code can then be relayed to the scanner.

The foregoing and other aspects of the invention will appear in the detailed description which follows. In the description, reference is made to the accompanying drawings which illustrate a preferred embodiment of the invention.

DESCRIPTION OF THE PREFERRED EMBODIMENT

Figure 1:
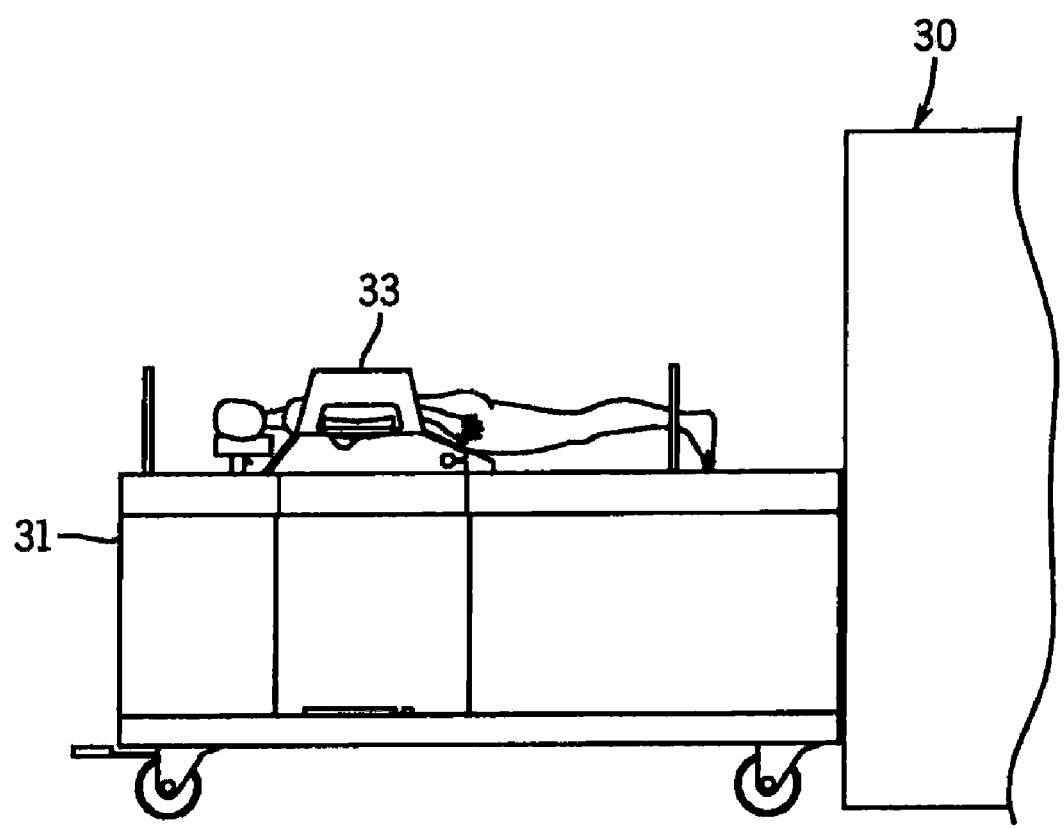
FIG. 1 is a perspective view of a patient supported on a patient transport adjacent a bore in an MRI system.

Referring to FIG. 1, the present invention is employed in an MRI system or scanner 30 of the type shown. The MRI system 30, as described above, includes a bore dimensioned to receive a patient for imaging. The patient lies on a patient transport 31, which can be, as shown here a wheeled structure. The patient is positioned on a tabletop sized to be received on the patient transport 31, and which can be selectively inserted into and removed from the bore. The transport 31 can also include a patient support 33 for supporting or immobilizing a specific portion of the anatomy to be imaged. As described below, the patient support 33 includes a plurality of connectors for receiving local RF coils at various positions on the support that are selected to provide imaging of the breast from a variety of angles and orientations. Although, as shown here, and as described below, the patient support 33 is configured for breast imaging, it will be apparent to those of ordinary skill in the art of that supports can be provided for many selected anatomical features. The configuration shown, therefore, is illustrative, and is not limiting.

Figure 2:
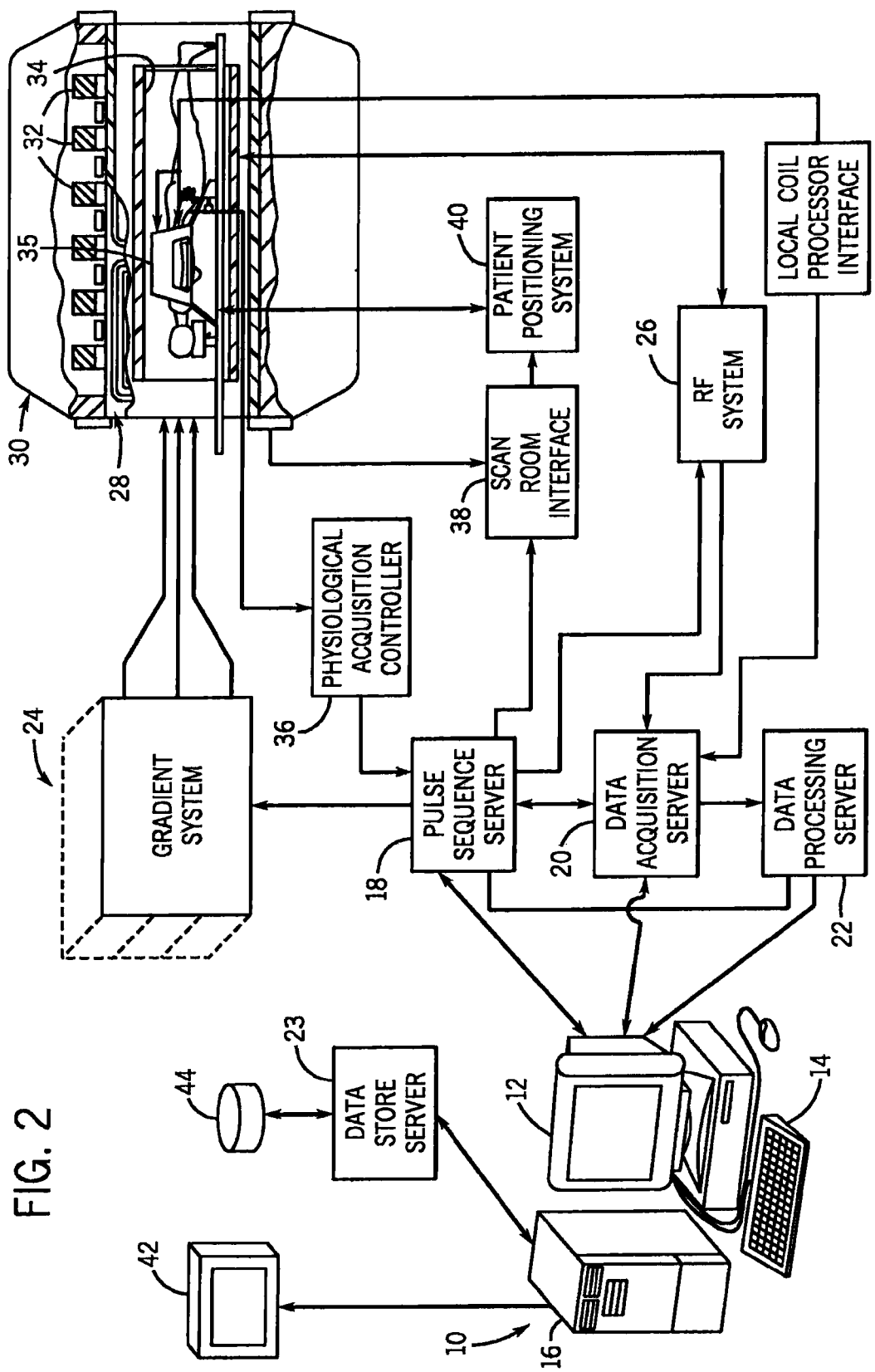
FIG. 2 is a block diagram of an MRI system implementing the present invention.

Referring now to FIG. 2, a typical MRI system 30 that can be used with the present invention is shown. The MRI system 30 includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to four servers including a pulse sequence server 18, a data acquisition server 20, a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$, and $G_z$ used for position encoding MR signals. The gradient coil assembly 28 forms part of a magnet assembly 30 that includes a polarizing magnet 32 and a whole-body RF coil 34.

RF excitation waveforms are applied to the RF coil 34 and/or to one or more local coil 35 by the RF system 26 to perform the prescribed magnetic resonance pulse sequence. Responsive MR signals detected by the RF coil 34 and/or the separate local coil 35 are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays 35.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. The data acquisition server 20 acquires MR data and processes it in real-time to produce information that is used to control the scan.

The data processing server 22 receives MR data from the data acquisition server 20 and processes the MR data in accordance with instructions downloaded from the workstation 10. Such processing may include, for example, Fourier transformation of raw k-space MR data to produce two or three-dimensional images, the application of filters to a reconstructed image, the performance of a backprojection image reconstruction of acquired MR data; the calculation of functional MR images, the calculation of motion or flow images, and the like.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 3:
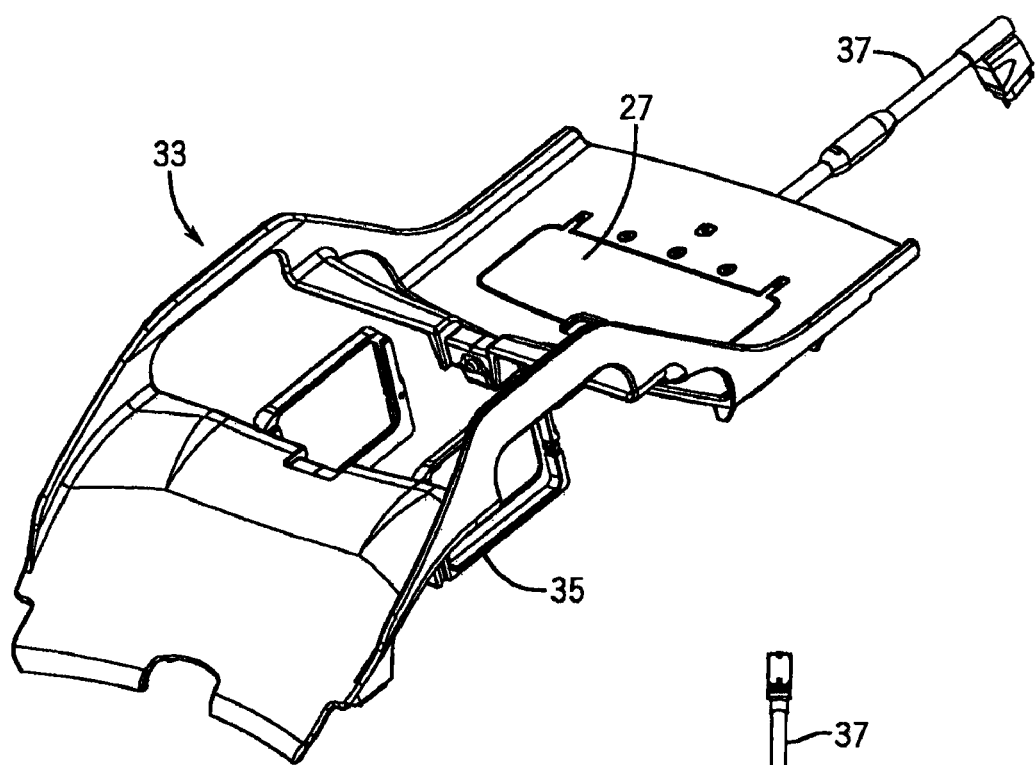
FIG. 3 is a perspective view of the patient support of FIG. 1 and corresponding local RF coils.
Figure 4:
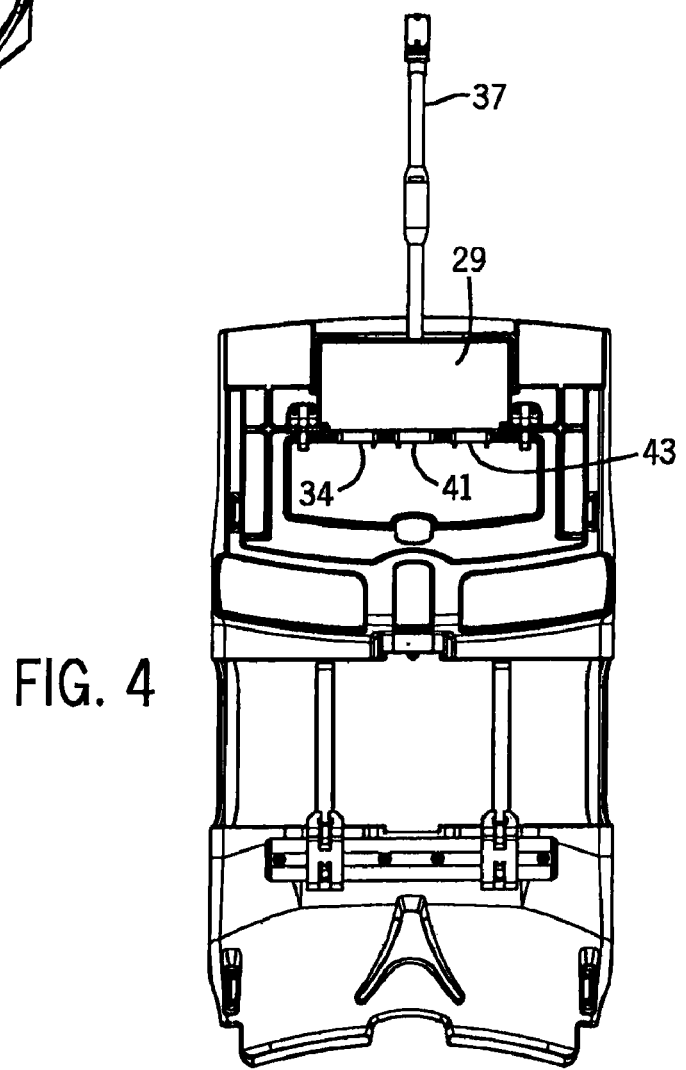
FIG. 4 is a bottom view of the patient support of FIG. 1.

Referring now to FIGS. 3 and 4, a perspective view and a bottom view of the patient support structure 33 are shown, respectively. As discussed above, the patient support structure 33 is designed specifically for positioning the breast for imaging, as described more fully in the co-pending patent applications entitled "OPEN ARCHITECTURE TABLETOP PATIENT SUPPORT AND COIL SYSTEM", filed on even day herewith as Ser. No. 12/277,061, which is hereby incorporated by reference, filed on even day herewith, which is hereby incorporated by reference for its description of this device. To provide access to the breast by local RF coils 35 during imaging, the patient support structure 33 includes an opening positioned between upward and downward ramps, which is dimensioned to receive the breasts of the patient pendant in the opening as can be seen, for example, in FIG. 1. Local RF coils 35 can be provided both medial to lateral (on the left and right sides) of the breast, and each of these coils is directed to a specific coil connector 39, 41 and 43 correlated to the left lateral, medial, and right lateral RF coils, respectively. The patient support structure 33 further includes a mounting element 27 for receiving a microprocessor module 29 which can be connected to the MRI scanner 30 through a connector 37. Signals for activating the RF coils 35 and for identifying the RF coils 35 connected to the patient support structure 33 are transmitted through the connector 37. Typical MRI coils convey identification codes to the MRI when connected. According to the present invention, a variety of different coils 35 may be connected to the coil connectors 39, 41 and 43. Discrete signal lines or other identification means such as keys or optical fibres in the connectors 39, 41 and 43 determine which coil is connected to which coil connector. The microprocessor distinguishes whether the connected coils correspond to a valid coil configuration, and if so, convey the appropriate coil identification code or signal to the scanner.

Alternatively, the microprocessor may be used to compute and/or convey other digital information to the scanner, including pulse sequence data for programming the pulse sequencer 18, or digitized signals derived from the analog (RF) imaging signals received from the coils. Alternatively, the microprocessor could be used to compute and convey diagnostic information concerning the state of the coils, or compare signal characteristics (such as noise) between imaging channels.

Figure 5:
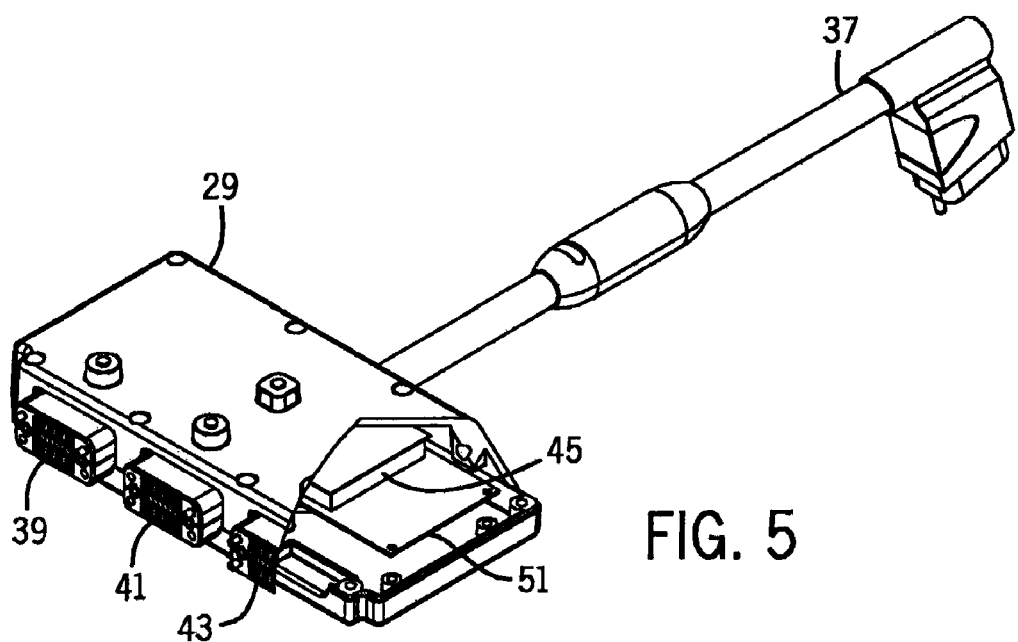
FIG. 5 is a cutaway view of a microprocessor module that is receivable in the patient support of FIG. 4.

Referring now to FIG. 5 a cut-away view of the microprocessor module 29 is shown. As can be seen here, the module 29 includes a housing 27 from which coil connectors 39, 41 and 43 are accessible on one side, and the connector 37 to the MRI system 30 is provided on the opposing side. A printed circuit board 51 is positioned inside the housing, which includes an interactive circuit for identifying the type and location of the local RF coils 35 connected to the patient support module 33, and for providing the identification to the MRI system 30.

Figure 6:
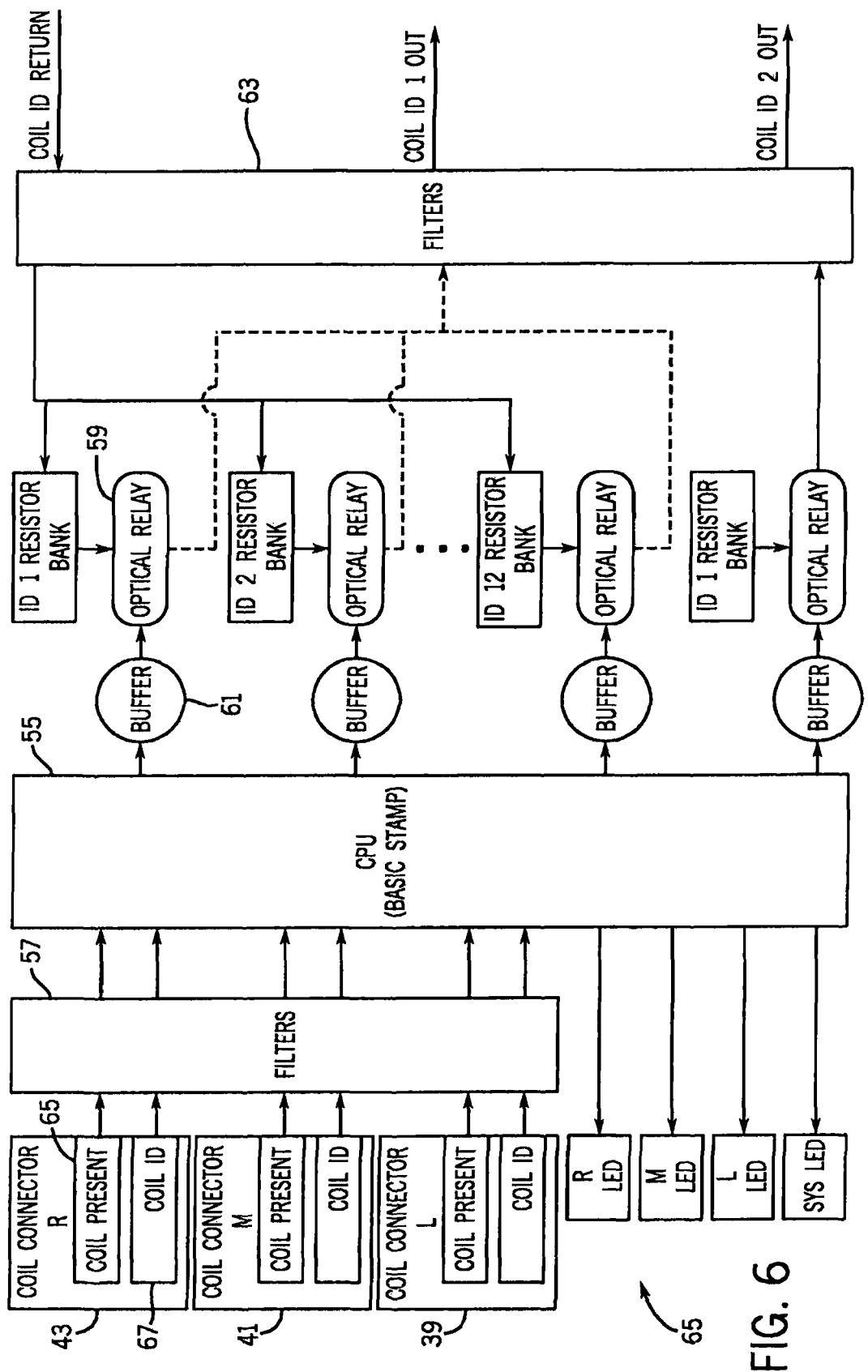
FIG. 6 is a block diagram illustrating an interface circuit for connection between local RF coils and the MRI system.

Referring now also to FIG. 6, a block diagram of the connections between the RF coils 35, printed circuit board 51, and MRI system 30 is shown. The printed circuit board 51 includes a microprocessor or microcontroller ("controller") 55 that is coupled to RF coil connectors 43, 41 and 39 through filters 57, and to the MRI system 30 through optical relays 59. One side of each of the optical relays 59 is coupled to the controller 55 through a buffer 61 which can be, for example, a transistor switch circuit and a filter 57. The opposing side of the relays 59 is routed through a second set of filters 63, to a connector that is configured to be connected to MRI system 30.

Referring still to FIG. 6, The coil connectors 39, 41, and 43 each include a sensor 65 that provides a signal indicating that an RF coil is connected to the corresponding connector. A coil identifier 67 is also associated with the RF coil to identify the type and configuration of the coil. The identifier may, for example, store a part number of the coil. Alternatively, a code indicating a type or coil configuration could also be provided. A plurality of LEDs 66 are selectively activated by the controller 55 to indicate which of the coil connectors 39, 41 and 43 have received an RF coil, or to provide an error signal, as described below. Although a number of different memory components can be used, the coil identifier 67 is preferably a single wire programmable memory device. An example of a suitable device is the DS2506 available from Dallas Semiconductors. When using this device, a protective component, such as the DS9503 ESD Protection Diode with Resistors, also available from Dallas Semiconductors, is preferably also used to limit electromagnetic interference.

Referring still to FIG. 6, a buffer 61 is provided between each optical relay 59 and the CPU 55, and together, the buffers 61 and optical relays 59 electrically isolate the controller 55 from connection to the MRI system 30. The optical relays 59 are connected between the MRI cable 37 and the controller 55 to limit common-mode noise from interaction devices the gradient and B1 field and the cable 37, and from differences in potential between the electronic circuits in the MRI system 30 and the printed circuit board 51.

Figure 7:
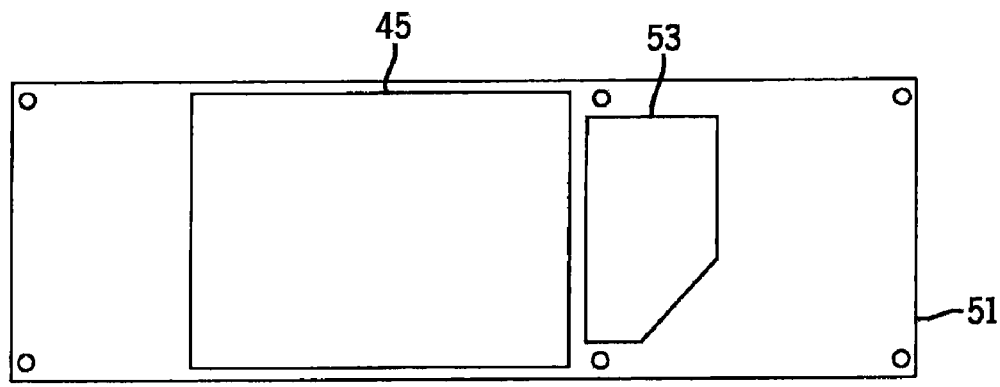
FIG. 7 is a top view of a circuit board in the interface circuit of FIG. 6.

Referring again to FIG. 5 and now also to FIG. 7, the printed circuit board 51 includes a shielded controller compartment 45 which is constructed from metallic foil material, and which is positioned over the controller 55 on circuit board 51. The shielded controller compartment 45 limits electromagnetic interference (EMI) and associated noise generated by the MRI system 30, and particularly the B1 field, from interfering with the operation of the controller 55, and also limits noise produced by the controller 55 from interfering with the MRI system 30 when used in bore.

Figure 8:
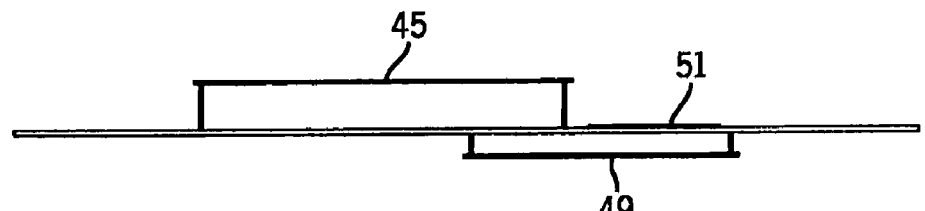
FIG. 8 is a side view of the circuit board of FIG. 6.

Referring still to FIG. 7 and now also to FIG. 8 the printed circuit board 51 is a two-sided board, and the optical relays 59 are mounted on opposing side of the board 51 from the controller 55. The optical relays 59 are also positioned in a foil-covered shielded optical relay compartment 49. The shielded controller compartment 45 and shielded optical relay compartment 49 are constructed of a conductive material, and are shielded in all directions. There is a continuous soldered connection at every joint and seam of the compartments 45 and 49 to prevent gaps in the shield.

In one embodiment, the compartments 45 and 49 are constructed from five pieces of double sided circuit board material, four providing walls and the fifth providing a roof of the compartment. The edges of each of the five pieces of circuit board material are wrapped in copper, which is soldered in position to provide conductivity from one side of the compartment to another. The four wall pieces are then tacked into position on the circuit board 51, and are then soldered in position to ensure that all of the seams are shielded. The fifth piece is then soldered onto the four wall pieces to form the enclosure. In alternative embodiments, the walls can be constructed using copper or brass components rather than circuit boards can also be used. Although a specific rectangular construction is described, it will be apparent that the shape of the enclosure is exemplary, and various enclosed configurations should be used.

Referring again to FIG. 7, signals into and out of the controller 55 are shielded through the filters 57, discussed above. To sufficiently filter the EMI noise on connections to and from the controller 55, the filters 57 are preferably ceramic feedthrough capacitors, such as those available from Tusonix of Tuscon, Ariz., and the capacitance value is selected to provide a low impedance path to ground for the RF noise. The filters 57 are retained in the compartments 45 and 49 to further limit noise to the controller 55.

Signals and power lines that enter and exit the shielded compartments 45 and 49 are routed through capacitive filters 63, preventing exposure to noise in the external environment. As shown in FIG. 7, communication lines to and from the circuit board 51 are also enclosed beneath a foil shield 53, thereby further limiting problems with noise.

Figure 9:
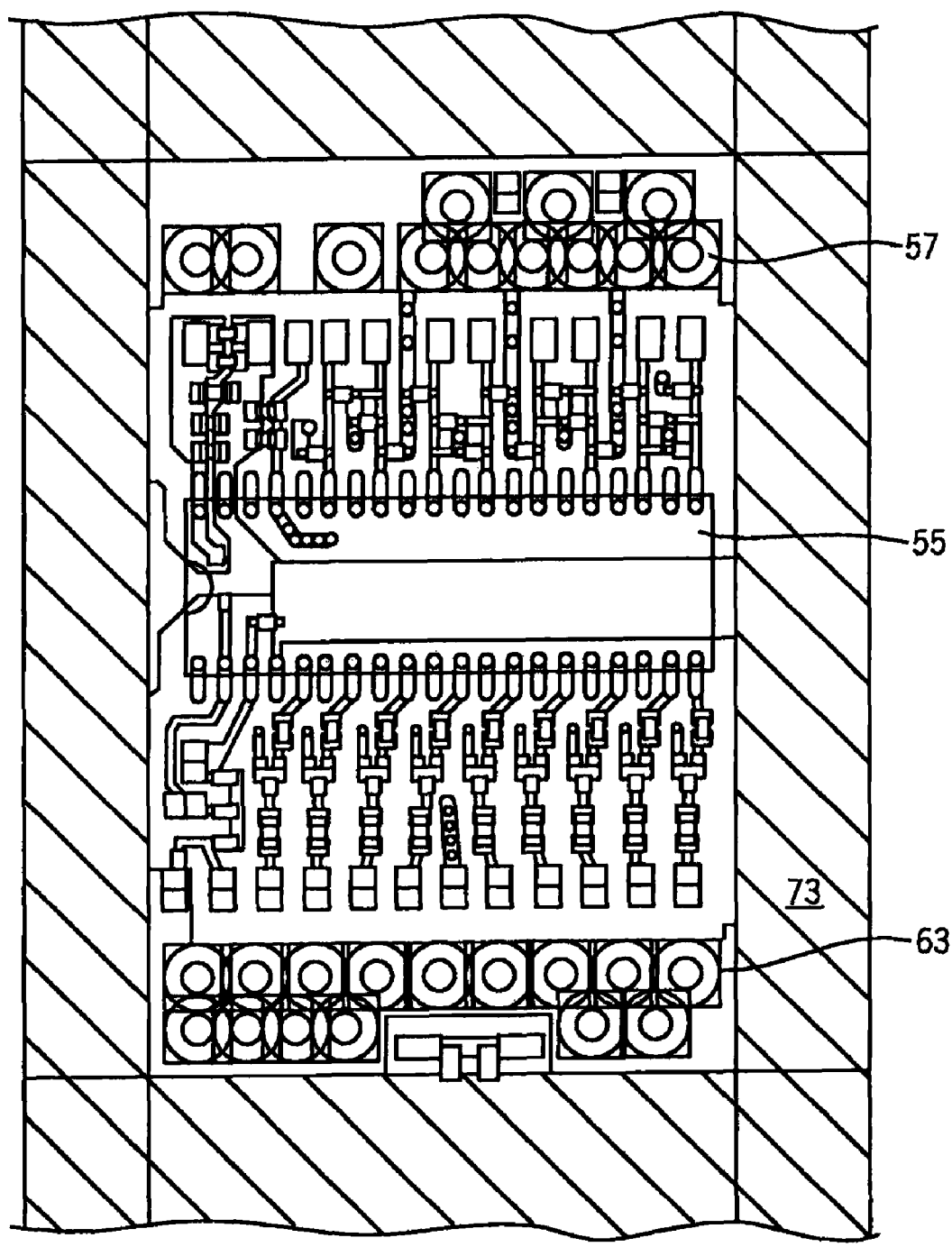
FIG. 9 is a layout drawing of the circuit board of FIG. 7 illustrating a portion of a top view.
Figure 10:
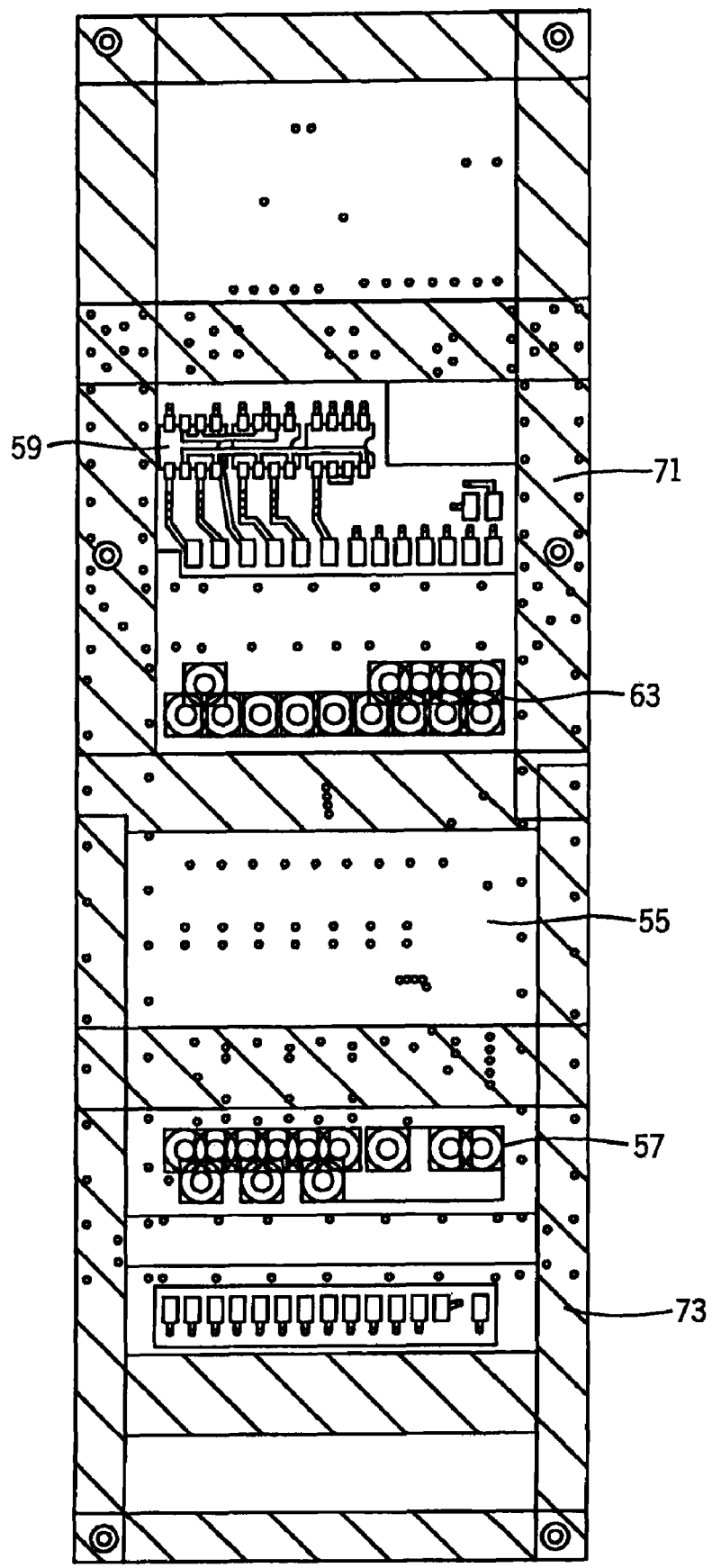
FIG. 10 is a layout drawing of the circuit board of FIG. 7 illustrating a bottom view.

Referring now to FIGS. 9 and 10, a portion of the top and a bottom layout of the printed circuit board 51 are shown, respectively. As described above, the shielded compartments 45 and 49 are formed on the printed circuit board 51, and are positioned to surround the controller 55 and optical relays or opto-coupling devices 59, respectively. To minimize interference from EMI, the return paths for signals and power are constructed to be geometrically coincident with their respective signal or power lines. The signal and power lines, moreover, are routed on the top and middle layers of the printed circuit board 51 within the shielded compartments 45 and 49. The bottom trace is solid copper, and the top and bottom ground planes 73 are joined by way of two double, continuous rows of vias 71 (more than one per centimeter), which connect the top and bottom ground planes to form a "picket fence" of vias. These vias equalize the potential on the top and bottom sides of the circuit board 51, and prevent a difference in potential between the top and bottom layers which would render shielding ineffective.

In operation, the controller 55 receives input signals from the sensors 65 associated with connectors 39, 41, and 43 which indicate that a coil has been received in the respective connector. When the sensor 65 indicates that a coil is present in a selected connector 39, 41, or 43, the controller 55 reads the identification data stored in the coil identifier 67. If the data acquired from the sensors 65 and 67 indicates that the configuration of coils in the connectors 39, 41, and 43 is not appropriate for the application, the controller 55 activates the indicator lights 66, indicating an error. For example, the controller 55 can cause the indicator lights 66 to blink, or activate a particular color or pattern of lights to indicate an error.

If the data acquired from the sensors 65 and 67 indicates that the configuration of coils in the connectors 39, 41, and 43 is appropriate for the application, the controller 55 selectively activates the buffers 61, which control the optical relays 59 to provide an output coil identification signal to the MRI system 30. The optical relays 59 can, for example, selectively short input lines from the magnet 30 to ground to provide a predetermined pattern of high and low input signals indicating an appropriate coil identification, or provide a return path to the MRI system 30 which can return, for example, a resistance value. In alternate embodiments, the controller 55 could provide a communication signal in a predetermined protocol to the MRI system 30. The protocol could, for example, mimic the protocol used in a single wire memory chip, or provide other types of communications. The output coil identification can be customized for the specific MRI system 30 being used.

It should be understood that the methods and apparatuses described above are only exemplary and do not limit the scope of the invention, and that various modifications could be made by those skilled in the art that would fall under the scope of the invention. To apprise the public of the scope of this invention, the following claims are made:

The invention claimed is:

1. An interface circuit for use in bore in a magnetic resonance imaging system, the interface circuit being electrically connected to circuitry in the magnetic resonance imaging system to enable communications between the interface circuit and the magnetic resonance imaging system, the interface circuit comprising:
   a controller;
   an isolation circuit electrically connected to the controller to isolate the controller from noise produced in the magnetic resonance imaging system;
   a feedthrough capacitor circuit, the feedthrough capacitor circuit filtering input and output lines to the controller;
   wherein the controller, the isolation circuit, and the feedthrough capacitor circuit are each positioned in a shielded compartment, such that electromagnetic interference is sufficiently minimized to allow communication signals to be transmitted between the microcontroller and the magnetic resonance system when the interface circuit is used in the bore of the magnetic resonance imaging system.

2. The interface circuit as recited in claim 1, wherein the isolation circuit comprises opto-electric coupling circuits.

3. The interface circuit as recited in claim 1, wherein at least a portion of the controller circuit is formed on a printed circuit board having a first and a second side, and the controller is provided on the first side of the board, and the isolation circuit is provided on the second side of the board, and wherein the shielded compartment comprises a first shielded compartment positioned over the controller on the first side of the printed circuit board, and a second shielded compartment positioned over the isolation circuit on the second side of the printed circuit board.

4. The interface circuit as recited in claim 1, wherein the shielded compartment comprises a metallic enclosure.

5. The interface circuit as recited in claim 1, further comprising an RF coil connectable to the microcontroller, wherein the RF coil includes a memory component for storing identification data that is readable by the controller to identify the RF coil.

6. The interface circuit as recited in claim 5, wherein the controller is programmed to read the identification data from the RF coil, and to evaluate whether the RF coil is suitable for a selected application of the MRI system.

7. A patient support for use in a magnetic resonance imaging system, the patient support comprising:
   a structure for supporting an anatomy of interest of a patient to be imaged;
   a connector for coupling an RF coil adjacent the anatomy of interest for imaging; and
   an interface circuit electrically connected to the connector, the interface circuit including a controller programmed to sense when an RF coil is coupled to the connector, and to read an identifier associated with the RF coil, wherein the controller circuit is shielded from electromagnetic interference produced by the magnetic resonance imaging system, and is programmed to determine whether the RF coil is suitable for use in the magnetic resonance imaging system.

8. The patient support as recited in claim 7, wherein the controller circuit is shielded by a metallic enclosure.

9. The patient support as recited in claim 7, wherein the interface circuit further comprises a plurality of indicator lights, and wherein the controller is programmed to activate at least one of the plurality of indicator lights when the controller determines that the RF coil is not suitable for use in the magnetic resonance imaging system.

10. The patient support as recited in claim 7, wherein the controller is shielded by a feedthrough capacitor circuit.

11. The patient support as recited in claim 7, further comprising an RF coil connectable to the microcontroller, wherein the RF coil includes a memory component for storing identification data that is readable by the controller to identify the RF coil.

12. The patient support as recited in claim 7, wherein the controller is further programmed to provide a coil identification signal to an MRI system coupled to the patient support.

13. The patient support as recited in claim 7, wherein the interface circuit is removably coupled to the patient support.

* * * * *